(12) United States Patent
Tsuzuki

(10) Patent No.: US 6,793,626 B2
(45) Date of Patent: Sep. 21, 2004

(54) ULTRASONIC SCATTERER, ULTRASONIC IMAGING METHOD AND ULTRASONIC IMAGING APPARATUS

(75) Inventor: Hirohiko Tsuzuki, Kanagawa (JP)

(73) Assignee: Fuji Photo Film Co., Ltd., Kanagawa (JP)

(*) Notice: Subject to any disclaimer, the term of this patent is extended or adjusted under 35 U.S.C. 154(b) by 72 days.

(21) Appl. No.: 10/046,740

(22) Filed: Jan. 17, 2002

(65) Prior Publication Data
US 2002/0129656 A1 Sep. 19, 2002

(30) Foreign Application Priority Data
Jan. 17, 2001 (JP) .................................. P.2001-008943
Jan. 17, 2001 (JP) .................................. P.2001-009063

(51) Int. Cl.⁷ .............................................. A06B 8/00
(52) U.S. Cl. ..................................................... 600/458
(58) Field of Search ................................ 600/437, 443, 600/447, 458; 128/916; 424/9.52

(56) References Cited

U.S. PATENT DOCUMENTS

| | | | |
|---|---|---|---|
| 5,215,680 A | * 6/1993 | D'Arrigo | 252/307 |
| 5,540,909 A | * 7/1996 | Schutt | 424/9.52 |
| 5,706,819 A | 1/1998 | Hwang et al. | |
| 5,855,865 A | 1/1999 | Lambert et al. | |
| 5,948,387 A | 9/1999 | Unger et al. | |
| 6,054,118 A | * 4/2000 | Ostensen | 424/9.52 |
| 6,080,386 A | 6/2000 | Porter | |

FOREIGN PATENT DOCUMENTS

| | | |
|---|---|---|
| JP | 9-164138 A | 6/1997 |
| JP | 10-505900 A | 6/1998 |
| JP | 11-178824 A | 7/1999 |
| JP | 2000-005167 A | 1/2000 |
| JP | 2000-501745 A | 2/2000 |
| JP | 2000-502047 A | 2/2000 |
| JP | 2000-506122 A | 5/2000 |

OTHER PUBLICATIONS

E. Leen, vol. 43, Issue 3, (Sep. 1999), pp. 17–22.
Peter J.A. Frinking et al., J. Acoust.Soc. Am., vol. 105(3), (Mar. 1999), pp. 1989–1996.
Paul A. Dayton et al., IEEE Transactions On Ultrasonics, Ferroelectrics, And Frequency Control, vol. 46, No. 1, (Jan. 1999), pp. 220–232.
Ayache Bouakaz et al., IEEE Ultrasonics Symposium, (1999), pp. 1693–1696.
Nicchoi Kiso Gijutsu Kenkyukai Shiryo, vol. 100, No. 2, pp. 29–34.
P.M. Shankar et al., J. Acoust. Soc. Am., vol. 106(4) Pt.1, (Oct. 1999), pp. 2104–2110.
Zhen Ye, J. Acoust. Soc. Am., vol. 100(4) Pt.1, (Oct. 1996), pp. 2011–2028.
Nico de Jong et al., 1ˢᵗ U.S. Contrast abstracts, (1999), pp. 29–30.
Nicchoi Kiso Gijutsu Kenkyukai Shiryo, vol. 100, No. 2, pp. 1–10.

* cited by examiner

*Primary Examiner*—Francis J. Jaworski
(74) *Attorney, Agent, or Firm*—Birch, Stewart, Kolasch & Birch, LLP

(57) ABSTRACT

The ultrasonic scatterer of the invention comprises gas-containing particles having an average particle size of 0.01 $\mu$m to 10 $\mu$m, the ultrasonic imaging method of the invention comprises transmitting an ultrasonic wave continuing for ten cycles or more; transmitting an ultrasonic wave continuing for four cycles or more and less than ten cycles after a predetermined period passes, and the ultrasonic imaging apparatus of the invention comprises transmitting means for sending a driving signal to the ultrasonic probe so as to transmit, to a subject, an ultrasonic wave continuing for four cycles or more and less than ten cycles after a predetermined period passes subsequently to transmitting, to the subject, of an ultrasonic wave continuing for ten cycles or more.

12 Claims, 10 Drawing Sheets

ULTRASONIC SCATTERER, ULTRASONIC IMAGING METHOD AND ULTRASONIC IMAGING APPARATUS

FIELD OF THE INVENTION

The present invention relates to an ultrasonic scatterer, ultrasonic imaging method and ultrasonic imaging apparatus, which highly ensure a generation of subharmonic echo. The present invention particularly relates to an ultrasonic scatterer that is useful as a contrast agent for ultrasonic diagnosis, to an ultrasonic imaging method and an ultrasonic imaging apparatus for detecting a sub-harmonic echo intensity by using a micro bubble contrast agent.

BACKGROUND OF THE INVENTION

In recent years, an ultrasonic diagnosis has been remarkably developed in a diagnosis of breast and abdomen portions because of such a feature that blood flow information can be acquired. In particular, an ultrasonic image pick-up technique using a contrast agent has been developed. Therefore, more accurate blood flow information has been acquired. In such an ultrasonic contrast, a micro bubble contrast agent including a large number of micro bubbles having a diameter of 1 to several $\mu m$, which are mixed into a liquid is mainly used with an injection into a vein. The micro bubble is obtained by filling a gas (air or carbon fluoride) which is non-toxic to an organism in a shell comprising a substance (lecithin) which is non-toxic to the organism.

JP-A-9-164138 (Japanese Patent Laid-Open No. 164138/1997) has described an ultrasonic diagnosis image processing method of injecting a micro bubble ultrasonic contrast agent into a blood flow and sending an ultrasonic pulse to break the micro bubble in a tissue, thereby measuring, through an ultrasonic wave, the extent of the recirculation of the micro bubble in the tissue at a certain time interval after the breakdown of the micro bubble.

Also in an ultrasonic image pick-up technique, moreover, a Doppler signal and a harmonic signal have been increasingly utilized so that blood flow information in more tissues can be acquired. In particular, a blood flow movement can be evaluated more accurately by a combination with ultrasonic contrast.

JP-A-11-178824 has described a pulse inversion Doppler ultrasonic diagnosis image processing method comprising the steps of transmitting a modulated ultrasonic sequence into a body to make a phase difference on an ultrasonic echo obtained as a response thereof, receiving a set of ultrasonic echo signals responding to the transmitted sequence, and analyzing the set to separate phase shift information about linear and non-linear signal components.

In the detection of such a Doppler signal, however, a large signal sent from a tissue having a great movement such as a heart muscle or a harmonic signal generated from the tissue itself is mixed. Therefore, it is impossible to singly detect a micro bubble in a blood vessel.

There has been investigated so-called sub-harmonic imaging in which an ultrasonic wave having a plurality of continuous waves is irradiated to generate an image based on a sub-harmonic echo generated from only the micro bubble in the blood vessel. A sub-harmonic component is generated by only the chaotic oscillation and branch phenomenon of the micro bubble. Therefore, it has been supposed that the sub-harmonic imaging can acquire a higher contrast than that of harmonic imaging.

U.S. Pat. No. 5,706,819 has described an ultrasonic diagnosis image processing method of injecting a harmonic contrast agent into a subject and mutually inverting the polarity of a transmitted pulse to combine a received echo signal, thereby suppressing the harmonic component of a transmitted signal and removing a scattering to detect the influence, of a harmonic contrast agent.

According to such a method, however, the sum of harmonics and sub-harmonics is detected. Therefore, the sub-harmonics cannot be detected singly.

Moreover, JP-A-2000-5167 has described an ultrasonic wave transmitting method of transmitting an ultrasonic wave including waves having an instantaneous sound pressure for breaking a micro balloon (a micro bubble) present respectively before and after at least one wave having an instantaneous sound pressure which does not break the micro balloon, in transmitting an ultrasonic wave having a plurality of continuous waves, and of reliably generating a sub-harmonic echo.

According to such a method, however, the micro balloon is broken. Therefore, it is impossible to continuously observe the micro balloon injected into a subject in a real time.

In recent years, furthermore, a mechanism for generating sub-harmonics has often been investigated. There has been known that ultrasonic waves having a plurality of continuous waves are irradiated to increase the intensity of sub-harmonics (Nico de Jong, First International Contrast Ultrasonic Wave Kyoto Symposium S1-1, Oct. 23, 1999).

In ultrasonic imaging, however, a space resolution is determined by the length of the transmitted continuous wave. Therefore, there is a problem in that the space resolution of an obtained ultrasonic image is reduced if an ultrasonic wave continuing for a long period is used.

As contrast agents for ultrasonic diagnosis, many ones are marketed or under clinical test. Examples thereof include Echovist®, Levovist® (Shering AG), Imagent® (Alliaancs Pharmaceutical Corp.), Optison™ (Molecular Biosystems, Inc.), EchoGen™ (SONUS Pharmaceutical, Inc.), Sonazoid™ (Nucomed Amershamplc), Definity™ (DuPont Pharmaceutical Co.), SonoVue™ (Bracco Diagnostics Inc.), Quantison™ (Quadrant Healthcare plc), etc. These contrast agents are stabilized microbubbles of several $\mu m$ in bubble size prepared by encapsulating the air or a gas of perfluorocarbon by a surfactant or a high molecular compound. These contrast agents have been developed mainly for keeping stability during storage as a chemical or in a blood liquid after injection, and techniques for enhancing strength of subharmonic are not employed therein.

In addition, with respect to the ultrasonic contrast agents, there have been disclosed a number of literature (for example, E. Leen, medicalmudi, 43(3), p.17 (1999); Nico de Jong and Folkert J. Ten Cate, Ultrasonics, 34, p.587 (1996); P. J. A. Frinking et al, J. Acoust. Soc., 105(3), p.1989 (1999); P. A. Dayton et al, IEE Trans. Ultrason., 46(1), p.220 (1999); and A. Bouakaz and K.K. Shung, 1999IEEE Ultrasonics Symposium, p.1963) and patents (U.S. Pat. Nos. 5,855,865, 6,080,386, 5,948,387, International Patent Publication No. 505900/1998, International Patent Publication No. 501745/2000, International Patent Publication No. 502047/2000 and International Patent Publication No. 506122/2000). However, methods for strengthening subharmonic have not yet been found.

The mechanism how subharmonic echo is generated from the microbubbles has not fully been explained theoretically, though many studies have been started. In the recent studies, it is inferred that bubbles are chaotically oscillated by irradiated ultrasound (Nicchoi Kiso Gijutsu Kenkyukai Shiryo, vol. 100, No. 2, p.29; P. M. Shankar et al, J. Acoust. Soc. Am., 106(4), 2014 (1999);Zhen Ye, J. Acoust. Soc. Am., 100(4), 2011 (1996); Nico de Jong et al, 1st US Contrast abstracts, p.29 (1999); etc.). Although analysis on oscillation of the microbubbles has proceeded in a dilute solution system, it has also been found that, in a high concentration region corresponding to the concentration of the actual ultrasonic contrast agent, there additionally appears a behavior as aggregates of microbubbles (bubble clouds), thus extrapolation of the dilute solution system being meaningless (Nicchoi Kiso Gijutsu Kenkyukai Shiryo, vol. 100, No. 2, p.1). That is, the subharmonic echo from the microbubbles is generated from the chaos of which the optimal region cannot theoretically be explained and its behavior is more complicated due to formation of the bubble clouds, thus an ultrasonic scatterer capable of generating a strong subharmonic echo not being defined unequivocally.

SUMMARY OF THE INVENTION

With these problems, the object of the invention is to provide an ultrasonic scatterer highly ensuring generation of subharmonic echo. In particular, the object of the invention is to provide an ultrasonic scatterer useful as an ultrasonic contrast agent which highly ensures generation of subharmonic echo under the conditions of not destroying the bubbles.

The another object of the invention is to provide an ultrasonic imaging method and an ultrasonic imaging apparatus in which a probability of the generation of a sub-harmonic component in the transmission of an ultrasonic wave is high and a sub-harmonic component included in an ultrasonic echo is detected at a speed close to a real time so that an image having an excellent space resolution can be obtained.

As a result of intensive investigations, the inventors have found that the above-described problems can be solved by the ultrasonic scatterer of the invention below.

(1) An ultrasonic scatterer comprising gas-containing particles having an average particle size of 0.01 $\mu$m to 10 $\mu$m, wherein, considering three adjacent articles including a first particle, the nearest particle to the first particle and the second nearest particle to the first particle, 20% to 100% by number of the total gas-containing particles satisfy that the three adjacent particles have a center-to-center distance between the first particle and the nearest particle of 0.01 $\mu$m to 10 $\mu$m, and a center-to-center distance between the first particle and the second nearest particle of 0.01 $\mu$m to 10 $\mu$m.

(2) An ultrasonic scatterer comprising gas-containing particles having an average particle size of 0.01 $\mu$m to 10 $\mu$m, wherein the gas-containing particles form particle aggregates including 3 to 100 continuous gas-containing particles, with the center-to-center distance between the gas-containing particles in the aggregates being 0.01 $\mu$m to 10 $\mu$m.

(3) The ultrasonic scatterer according to item (2), wherein the aggregates do not define a straight line when a line is drawn by connecting the centers of respective particles in the aggregates.

(4) The ultrasonic scatterer according to item (1), wherein, when diluted with pure water so that the average particle-to-particle distance of the gas-containing particles becomes 1 mm, 10% to 100% by number of the total gas-containing particles satisfy that the three adjacent particles have a center-to-center distance between the first particle and the nearest particle of 0.01 $\mu$m to 10 $\mu$m and a center-to-center distance between the first particle and the second nearest particle of 0.01 $\mu$m to 10 $\mu$m.

(5) The ultrasonic scatterer according to item (2), wherein, when diluted with pure water so that the average particle-to-particle distance of the gas-containing particles becomes 1 mm, 10% to 100% by number of the total gas-containing particles satisfy that the three adjacent particles have a center-to-center distance between the first particle and the nearest particle of 0.01 $\mu$m to 10 $\mu$m and a center-to-center distance between the first particle and the second nearest particle of 0.01 $\mu$m to 10 $\mu$m.

(6) The ultrasonic scatterer according to item (1), wherein, in 10 to 100% by number of the total gas-containing particles, the first particle and the nearest particle are positioned so as to not form a contact surface.

(7) The ultrasonic scatterer according to item (2), wherein the first particle and the nearest particle are positioned so as to not form a contact surface in 10 to 100% by number of the total gas-containing particles.

(8) An ultrasonic scatterer comprising:
gas-containing particles having an average particle size of 0.01 $\mu$m to 10 $\mu$m; and
at least one of inorganic solid fine particles and organic solid fine particles, each of which has an average particle size of 0.01 $\mu$m to 1 $\mu$m.

(9) The ultrasonic scatterer according to item (8), wherein, considering two adjacent particles including a first particle and the nearest particle to the first particle, 20% to 100% of the total gas-containing particles satisfy that the two adjacent particles have a center-to-center distance between the first particle and the nearest particle of 0.01 $\mu$m to 10 $\mu$m.

(10) The ultrasonic scatterer according to item (8), wherein, when diluted with pure water so that the average particle-to-particle distance of the gas-containing particles becomes 1 mm, 10% to 100% by number of the total gas-containing particles satisfy that the two adjacent particles have a center-to-center distance between the first particle and the nearest particle of 0.01 $\mu$m to 10 $\mu$m.

(11) The ultrasonic scatterer according to item (1), wherein the average particle size of the gas-containing particles is equal to or smaller than the center-to-center distance of the gas-containing particles.

(12) The ultrasonic scatterer according to item (2), wherein the average particle size of the gas-containing particles is equal to or smaller than the center-to-center distance of the gas-containing particles.

(13) The ultrasonic scatterer according to item (9), wherein the average particle size of the gas-containing particles is equal to or smaller than the center-to-center distance of the gas-containing particles, In order to solve the problem described above, the invention provides an ultrasonic imaging method comprising the steps of:
(a) transmitting, to a subject, an ultrasonic wave continuing for ten cycles or more;
(b) transmitting, to the subject, an ultrasonic wave continuing for four cycles or more and less than ten cycles after a predetermined period passes subsequently to the step (a);
(c) receiving an ultrasonic echo generated by reflecting the ultrasonic wave transmitted at the step (b) from the subject, thereby acquiring a detection signal; and (d) extracting a sub-harmonic component from the ultrasonic echo based on the detection signal.

Moreover, the present invention provides an ultrasonic imaging apparatus comprising:

an ultrasonic probe having a plurality of arranged ultrasonic transducers;

transmitting means for sending a driving signal to the ultrasonic probe so as to transmit, to a subject, an ultrasonic wave continuing for four cycles or more and less than ten cycles after a predetermined period passes subsequently to transmitting, to the subject, of an ultrasonic wave continuing for ten cycles or more;

receiving means for receiving, by the ultrasonic probe, an echo generated by reflecting, from the subject, the ultrasonic wave continuing for four cycles or more and less than ten cycles, thereby acquiring a detection signal; and signal processing means for extracting a sub-harmonic component from an ultrasonic echo based on the detection signal.

According to the structure described above, the ultrasonic wave continuing for ten cycles or more is transmitted to the subject. Consequently, the chaos oscillation or branch phenomenon of a micro bubble is activated to increase a probability of the generation of the sub-harmonic component, and the ultrasonic wave continuing for four cycles or more and less than ten cycles is then transmitted to the subject, thereby detecting the sub-harmonic component included in the ultrasonic echo at a speed close to a real time. Consequently, it is possible to obtain an image having an excellent space resolution.

Figure 1:
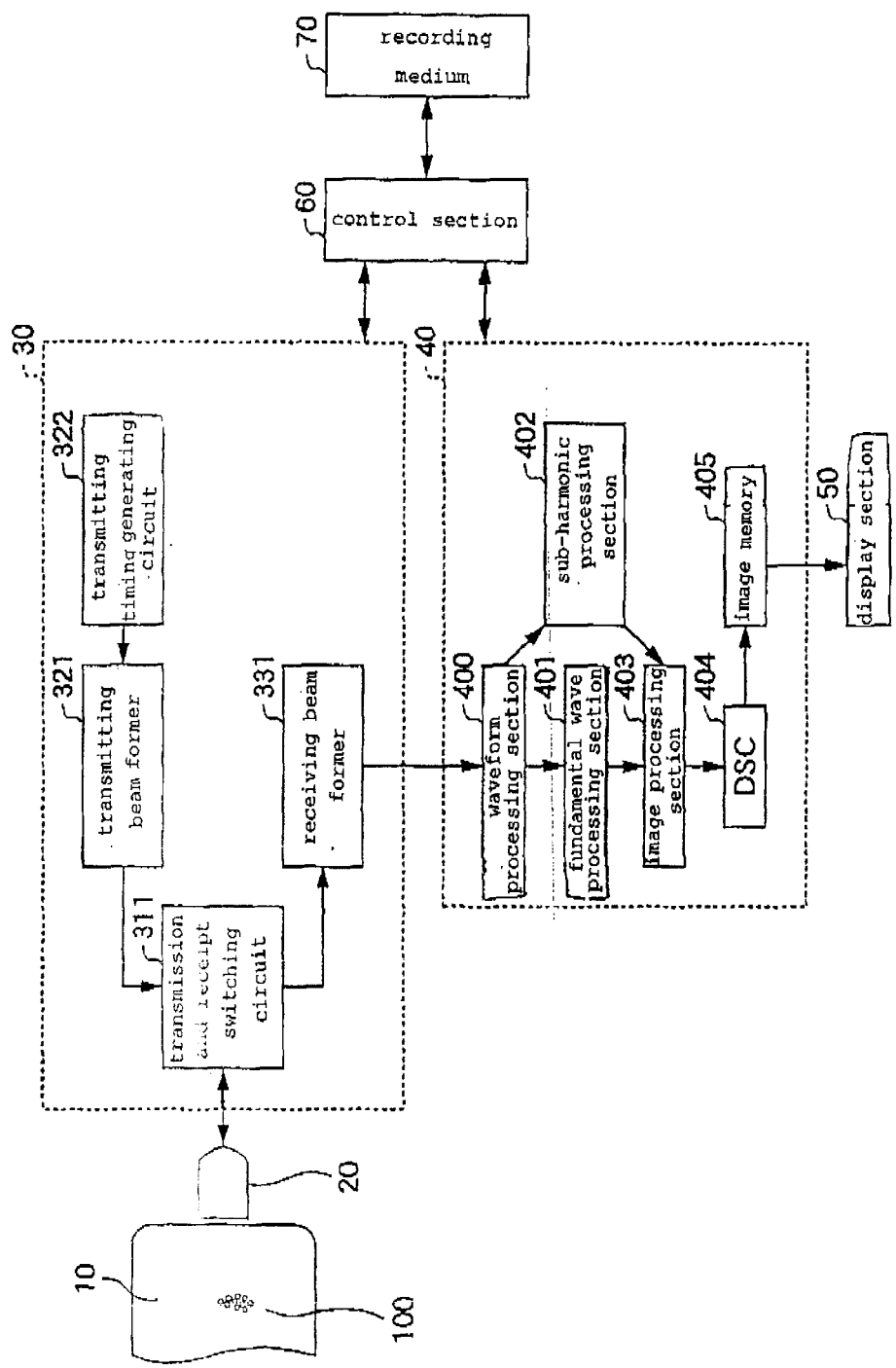
FIG. 1 is a block diagram showing the structure of an ultrasonic imaging apparatus according to a first embodiment of the invention.

1: delay circuit
2: differential circuit
10: subject
20: ultrasonic probe
30: transmitting and receiving section
40: signal processing section
50: display section
60: control section
70: recording medium
100: micro bubble
110: display of display section
111: tomogram image of tissue obtained based on fundamental wave echo
112: image obtained based on sub-harmonic echo of micro bubble
200: radiant point
202: sound ray
204: locus
206: two-dimensional region
208: divergent point
311: transmission and receipt switching circuit
321: transmitting beam former
322: transmitting timing generating circuit
331: receiving beam former
400: waveform processing section
401: fundamental wave processing section
402: sub-harmonic processing section
403: image processing section
404: digital scan converter (DSC)
405: image memory
910: luminance signal $X_0$
911: scattering of tissue a
912, 913: scattering of two walls of tissue b
914: scattering of tissue c
915: scattering of micro bubble injected into tissue b
920: luminance signal $X_{SUB}$
925: sub-harmonic signal of micro bubble injected into tissue b
501: water bath
502: pure water
511: agar cell
513: dispersion of an ultrasonic scatterer
521: transducer
522: arbitrary wave form-generating apparatus
523: hydrophone
524: oscilloscope
525: computer

DETAILED DESCRIPTION OF THE INVENTION

The ultrasonic scatterer of the invention is described in detail below. Additionally, in the specification of the invention, "a to b" means the range wherein "a" is the minimum value and "b" is the maximum value, both inclusive.

The gas-containing particles constituting the ultrasonic scatterer of the invention may be any one that can scatter ultrasonic wave. The average particle size thereof is 0.01 μm to 10 μm in terms of the average value of diameters of corresponding circles. In particular, in the case of using the ultrasonic scatterer of the invention as a contrast agent for ultrasonic diagnosis, the average particle size is preferably 0.1 μm to 10 μm.

It is common to intravenously inject the contrast agent for ultrasonic diagnosis into human body and conduct diagnosis when the contrast agent reaches the diseased part. In case where the contrast agent of the ultrasonic scatterer is too large, peripheral blood vessels can be occluded and, in case where too small, strength of the signal from the contrast agent becomes so near the strength of the signal from the natural ultrasonic scatterers within the living body such as blood corpuscles that analysis of the obtained echo signals becomes difficult.

The method for determining the particle size of the gas-containing particles is described below. A dispersion of the gas-containing particles is spread on a slide glass, a cover glass is placed thereon with a clearance of 10 μm to 100 μm, and the particles are observed and measured under an optical microscope or a digital microscope. As the number of particles for measuring the diameter, 200 or more is preferred in order to minimize statistical errors, with 600 or more being more preferred.

The material for the ultrasonic scatterer of the invention may be any one that is different in acoustic impedance from the dispersion medium and liquids into which the ultrasonic scatterer is to be injected, such as water or blood. The material includes a gas, gas-containing particles, particles capable of vaporizing at a temperature of the liquid into which the ultrasonic scatterer is injected, and particles capable of being evaporated by irradiation with ultrasonic waves.

Examples of the gas to be used in the invention includes air; nitrogen; oxygen; carbon dioxide; hydrogen; nitrous oxide; an inert gas such as helium, argon, xenon or krypton; sulfur fluoride such as sulfur hexafluoride, sulfur pentafluoride or trifluoromethylsulfur pentafluoride; selenium hexafluoride; optionally halogenated silane such as tetramethylsilane; a low molecular hydrocarbon (e.g., containing up to 7 carbon atoms) such as an alkane (e.g., methane, ethane, propane, butane or pentane), a cycloalkane (e.g., cyclobutane or cyclopentane), an alkene (e.g., propene or butene) or an alkyne (e.g., acetylene); an ether; a ketone; an ester; a halogenated low molecular hydrocarbon (e.g., containing up to 7 carbon atoms); and a mixture of these compounds. At least several halogen atoms in the halogenated gases are preferably fluorine atoms. Therefore, biologically acceptable halogenated hydrocarbon gases can be selected from among, for example, bromochlorodifluoromethane, chlorodifluoromethane, dichlorodifluoromethane, bromotrifluoromethane, chlorotrifluoromethane, chloropentafluoroethane, dichlorotetrafluoroethane and perfluorocarbons such as perfluoroalkanes (e.g., perfluoromethane, perfluoroethane, perfluoropropane, perfluorobutane (e.g., perfluoro-n-butane optionally mixed with other isomer such as perfluoroisobutane), perfluoropentane, perfluorohexane and perfluoroheptane); perfluoroalkenes (e.g., perfluoropropene, perfluorobutene (e.g., perfluorobut-2-ene) and perfluorobutadiene); perfluoroalkynes (e.g., perfluorobut-2-yne); and perfluorocycloalkanes (e.g., perfluorocyclobutane, perfluoromethylcyclobutane, perfluorodimethylcyclobutane, perfluorotrimethylcyclobutane, perfluorocyclopentane, perfluoromethylcyclopentane, perfluorodimethylcyclopentane, perfluorocyclohexane, perfluoromethylcyclohexane and perfluorocycloheptane). Other halogenated gases include fluorinated, for example, perfluorinated ketones such as perfluoroacetone and fluorinated, for example, perfluorinated ethers such as perfluorodiethyl ether.

Particularly preferred gases include perfluoroalkanes, particularly perfluoropropane, perfluorobutane, perfluoropentane and perfluorohexane.

In the invention, the gas is preferably stabilized by a shell. The shell material may be any of surfactants, natural or synthetic high molecular compounds, biphillic substances, etc. but, for the use as a contrast agent for ultrasonic diagnosis, so-called biologically acceptable compounds are preferred, with those which do not cause coagulation of blood when in contact with blood being more preferred. Those which are biodegradable are particularly preferred.

Specific examples of the shell material to be used in the invention are shown below which, however, are not limitative at all. The biphillic substances include phospholipids (e.g., lecithin, dipalmitoylphosphatidylcholine, sodium dipalmitoylphosphatidylate, dipalmitoylphosphatidyl ethanolamine polyethylene glycol ether, etc.), higher carboxylic acids (e.g., lauric acid, sodium laurate, palmitic acid, potassium palpitate, stearic acid, arachidic acid, behenic acid, etc.), higher alcohols (e.g., stearyl alcohol, palmitoyl alcohol, etc.), higher amines (e.g., stearylamine), etc. The high molecular compounds include natural high molecular compounds (e.g., gelatin, collagen, albumin, chitosan, agar, silkfibroin, starch, cellulose, dextran, etc.), chemically modified natural high polymers (e.g., acetylated gelatine, phthaloylated gelatin, enzyme-decomposed low molecular gelatine, hydroxypropyl cellulose, hydroxypropyl methyl cellulose, carboxymethyl cellulose, etc.) and synthetic high molecular compounds (e.g., polylactic acid, lactic acid-butryric acid copolymer, polyvinyl alcohol, polyethylene glycol, polyethylene glycol-propylene glycol copolymer, urea resin, nylon, polyacrylic acid, polyethylene glycol ester, etc.). The surfactants include anionic surfactants (e.g., sodium dodecylsulfonate, diisobutyl sulfosuccinate, sodium dodecylbenzenesulfonate, etc.), nonionic surfactants (e.g., low molecular weight polyethylene glycol, nonylphenol polyethylene glycol, low molecular polyethylene glycol-propylene glycol copolymer, alkyl modified sugars, etc.), cationic surfactants and fluorine-containing surfactants. These may be used alone or in combination of two or more of them.

In the invention, the shell material is preferably stabilized by crosslinking or denaturation. Such stabilization may be conducted by any means including chemical reaction, heat, UV ray irradiation, irradiation with a radiation, etc.

The dispersion medium for the dispersion of the ultrasonic scatterer in accordance with the invention may be any one that does not change the ultrasonic scatterer with time. In the case of using it as a contrast agent for ultrasonic diagnosis, the medium preferably contains a physiological salt solution as a major component. For the purpose of adjusting viscosity, a polyhydric alcohol (e.g., glycerin, propylene glycol or ethylene glycol), a sugar (e.g., glucose or fructose), a polysaccharide (e.g., dextran) or a water-soluble high polymer (e.g. polyvinyl, gelatin or albumin) may be added to the medium.

In the gas-containing particles of the invention, 20% to 100% by number of the total gas-containing particle, preferably 30% or more of the particles, still more preferably 50% or more of the particles, satisfy that a center-to-center distance between the first particle and the nearest particle and a center-to-center distance between the first particle and the second nearest particle are in the range of from 0.01 $\mu$m to 10 $\mu$m.

The method for determining the center-to-center distance between the first particle and the nearest particle and the center-to-center distance between the first particle and the second nearest particle in the gas-containing particles of the invention is described below. A dispersion of the gas-containing particles is spread on a slide glass, a cover glass is placed thereon with a clearance of 10 m to 100 $\mu$m, and central coordinates of each particle is determined by means of an optical microscope or a digital microscope. As the cover glass-placing method, there may preferably been employed a method of using a combination of a cover glass having a previously formed gap so as to form a uniform clearance between the slide glass and the cover glass (Gap Cover Glass; made by Matsunami Garasu Kogyo K.K.) and a slide glass or a method of injecting a liquid into the gap previously formed between the cover glass and the slide glass (Sekisui Kenkyo Plate; made by Sekisui Kagaku Kogyo K.K.) The second nearest particle to each of the particles is searched to calculate the distance therebetween based on the central coordinates thereof, and the ratio of the number of particles having the distance of 10 $\mu$m or less to the number of the total particles is calculated. In order to minimize statistical errors, the number of the particles to be measured is preferably 200 or more, with 600 or more being more preferred.

Additionally, with the ultrasonic scatterer of the invention, in the case of using the gas-containing particles of 0.01 $\mu$m to 10 $\mu$m in average particle size in combination with inorganic or organic solid fine particles of 0.01 $\mu$m to 1 $\mu$m in average particle size, the center-to-center distance to the second nearest particle may not be considered.

The gas-containing particles of the invention may form aggregates comprising 3 to 100 continuous particles, with the center-to-center distance being 0.01 $\mu$m to 10 $\mu$m. In this case, the line drawn by connecting the centers of respective particles constituting the aggregates is preferably not a straight line. The method or evaluating the straight properties or linearity of the line is as follows. First, a particle aggregate formed by the particles connecting to each other in the relation of 0.01 $\mu$m to 10 $\mu$m in the center-to-center distance is selected based on the central coordinates determined by the above-described method. Then, the relation with the central coordinates is approximated by straight lines to determine the coefficient of correlation. Aggregates having an average of the obtained coefficient of correlation of less than 90% are determined to be non-straight with respect to the line drawn by connecting the centers of respective particles constituting the aggregates.

Further, as the ultrasonic scatterers, those in which 10% to 100% by number of the total gas-containing particle satisfy that, when diluted with pure water so that the average particle-to-particle distance of the gas-containing particles becomes 1 mm, center-to-center distance between the first particle and the nearest particle and center-to-center distance between the first particle and the second nearest particle are in the range of from 0.01 $\mu$m to 10 $\mu$m are preferred, with 20% or more being more preferred.

The method for diluting with pure water so that the average distance between the particles becomes 1 mm is described below. First, the number of the particles per unit volume (n particles/ml) is determined based on observation under an optical microscope, and the occupied volume (V ml) is calculated by dividing the volume by the number of the particles.

In the case of the closest packing, relation between the occupied volume and the center-to-center distance between the near particles (L cm) is represented by the following formula:

$$V \times 0.641 = 4/3 \times \pi \times (L/2)^3$$

Here, a volume V is determined in the case of L being 1 mm, and the value calculated by dividing V by Vo is the dilution ratio for adjusting the center-to-center distance to be 1 mm.

In the gas-containing particles of the invention, the first particle and the nearest particle are positioned so as to not form a contact surface (an intermediate layer), in 10 to 100% by, number, preferably 20% or more of the total gas-containing particles.

The gas containing particles may be prepared by a conventional method, e.g., there are illustrated a method of injecting a predetermined gas into surfactant solution, a method of injecting a predetermined gas into a dispersion of a biphillic substance vehicle, a method of polymerizing a monomer in a liquid dispersed a gas, a method of adding solvent such as water to soluble powder containing a surfactant or a biphillic substance, a method of mixing a gas and liquid by a micronozzle or a micromixer, though not limitative at all. The obtained gas-containing particle may be subject to a classification using a filter and like to uniform a particle size.

As methods for shortening the distance between the gas-containing particles of the invention, there are Illustrated a method of adding a compound having 2 or more functional groups capable of forming an ion complex or a chemical bond with the shell of the bubbles, and a method of adding solid fine particles to thereby joining the solid particles to the gas-containing particles due to reduction in the surface energy, with the method of adding solid fine particles being preferred.

The inorganic or organic solid fine particles of the invention having an average particle size of 0.01 $\mu$m to 1 $\mu$m are described below.

The method for measuring particle size of the solid fine particles may be any of directly observing methods using, for example, an electron microscope or an optical microscope, a method of using a laser-scattering granulometer, and the like.

Compounds for forming the solid particles may be any of organic materials, inorganic materials and organic-inorganic composite materials. However, it is necessary for the materials to be solid in water, and organic high molecular compounds are preferably used. The term "solid" as used herein means to have a low solubility in water, and so-called hydrogels which allow impregnation with water but do not dissolve in water, micelles and liposomes are also included.

Examples of the organic materials for forming the solid particles of the invention include low molecular compounds, aggregates of low molecular compounds, high molecular compounds, etc., with an aggregate of a low molecular compound or a high molecular compound being preferred. The high molecular compound is particularly preferred.

As the aggregate of a low molecular compound, there are illustrated micelles of a surfactant and a vehicle comprising a biphillic substance such as liposome. The biphillic substances include phospholipids (e.g., lecithin, dipalmitoylphosphatidylcholine, sodium dipalmitoylphosphatidylate, dipalmitoylphosphatidyl ethanolamine polyethylene glycol ether, etc.), higher carboxylic acids (e.g., lauric acid, sodium laurate, palmitic acid, potassium palmitate, stearic acid, arachidic acid, behenic acid, etc.), higher alcohols (e.g., stearyl alcohol, palmitoyl alcohol, etc.), higher amines (e.g., stearylamine), etc., and the surfactants include anionic surfactants (e.g., sodium dodecylsulfonate, diisobutyl sulfosuccinate, sodium dodecylbenzenesulfonate, etc.), nonionic surfactants (e.g., low molecular weight polyethylene glycol, nonylphenol polyethylene glycol, low molecular polyethylene glycol-propylene glycol copolymer, alkyl modified sugars, etc.), cationic surfactants and fluorine-containing surfactants, though not limitative at all. These biphillic substances and surfactants may be used alone or in combination of two or more of them, or may be stabilized by crosslinking or denaturation by the technique of employing chemical reaction, heat, UV ray or radiation.

The high molecular compounds include natural high molecular compounds (e.g., gelatin, collagen, albumin, chitosan, agar, silkfibroin, starch, cellulose, dextran, etc.) chemically modified natural high polymers (e.g., acetylated gelatine, phthaloylated gelatin, enzyme-decomposed low molecular gelatine, hydroxypropyl cellulose, hydroxypropylmethyl cellulose, carboxymethyl cellulose, etc.) and synthetic high molecular compounds (e.g., polylactic acid, lactic acid-butryric acid copolymer, polyvinyl alcohol, polyethylene glycol, polyethylene glycol-propylene glycol copolymer, urea resin, nylon, polyacrylic acid, polyethylene glycol ester, SBR latex, polystyrene, PET, etc.), which are not limitative at all. The high polymers may be stabilized by crosslinking or denaturation which may be conducted by any means such as chemical reaction, heat, UV ray irradiation or irradiation with radiation.

Examples of the inorganic materials for forming the solid particles of the invention include metal oxides (e.g., colloidal silica, alumina, ferrite, etc.), composite oxides (e.g., colloidal silica surface-modified with alumina, zeolite, sellaite, etc.), metal colloids (e.g., silver colloid, gold colloid, etc.), slightly soluble phosphates (e.g., calcium phosphate, hydroxyapatite, etc.) and slightly soluble carbonates (e.g., calcium carbonates), though not limitative at all. The inorganic materials forming the solid particles of the invention may form a composite with the above-described organic compound.

In the case of using the ultrasonic scatterer of the invention as a contrast agent for ultrasonic diagnosis, the inorganic or organic solid fine particles are preferably formed by so-called biodegradable materials.

In the method of obtaining images using ultrasonic echo, the ultrasonic scatterer of the invention is used for confirming the stream by injecting into a liquid portion. In particular, it is favorably used as a contrast agent for ultrasonic diagnosis.

The method for obtaining ultrasonic echo of the invention may be any one, but the subharmonic echo method is effective for obtaining the remarkable effects of the invention.

Embodiments of the method and the apparatus in the invention will be described below in detail with reference to the drawings.

FIG. 1 is a block diagram showing the structure of an ultrasonic imaging apparatus according to a first embodiment of the invention.

As shown in FIG. 1, the ultrasonic imaging apparatus comprises an ultrasonic probe 20 including an ultrasonic transducer array constituted by a plurality of ultrasonic transducers. The ultrasonic probe 20 is used in abutment on a subject 10 by an operator. By previous injection of a micro bubble contrast agent, the subject 10 includes a micro bubble 100.

The ultrasonic probe 20 is connected to a transmitting and receiving section 30. In the transmitting and receiving section 30, a transmitting timing generating circuit 322 periodically generates a transmitting timing signal and sends the transmitting timing signal to a transmitting beam former 321. The transmitting beam former 321 generates a plurality of driving signals (transmitting beam forming signals) for driving a plurality of ultrasonic transducers of the ultrasonic probe 20 with a time difference based on the transmitting timing signal and sends the driving signals to the ultrasonic probe 20 through a transmission and receipt switching circuit 311. The waveforms of the driving signals are selected to have the sound pressure waveforms described below of a transmitting ultrasonic wave. A plurality of ultrasonic transducers constituting a transmitting aperture of the ultrasonic probe 20 transmit, toward the subject 10, a plurality of ultrasonic waves having a phase difference corresponding to the time difference of the driving signals. By such a wave front synthesis of the ultrasonic waves, an ultrasonic beam is formed.

On the other hand, the ultrasonic probe 20 receives an ultrasonic wave (echo) reflected from the subject 10 and converts the ultrasonic wave into an electric signal, and outputs the electric signal to a receiving beam former 331 through the transmission and receipt switching circuit 311. Thus, a plurality of echo signals received by the ultrasonic transducers constituting the receiving aperture of the ultrasonic probe 20 are input to the receiving beam former 331. The receiving beam former 331 gives a time difference to a plurality of received echoes to adjust a phase and then adds them, thereby forming an echo detection signal along a sound ray, that is, carrying out the beam forming of the received wave. By the receiving, beam former 331, the sound ray of the received wave is also scanned together with the transmitted wave.

Figure 2:
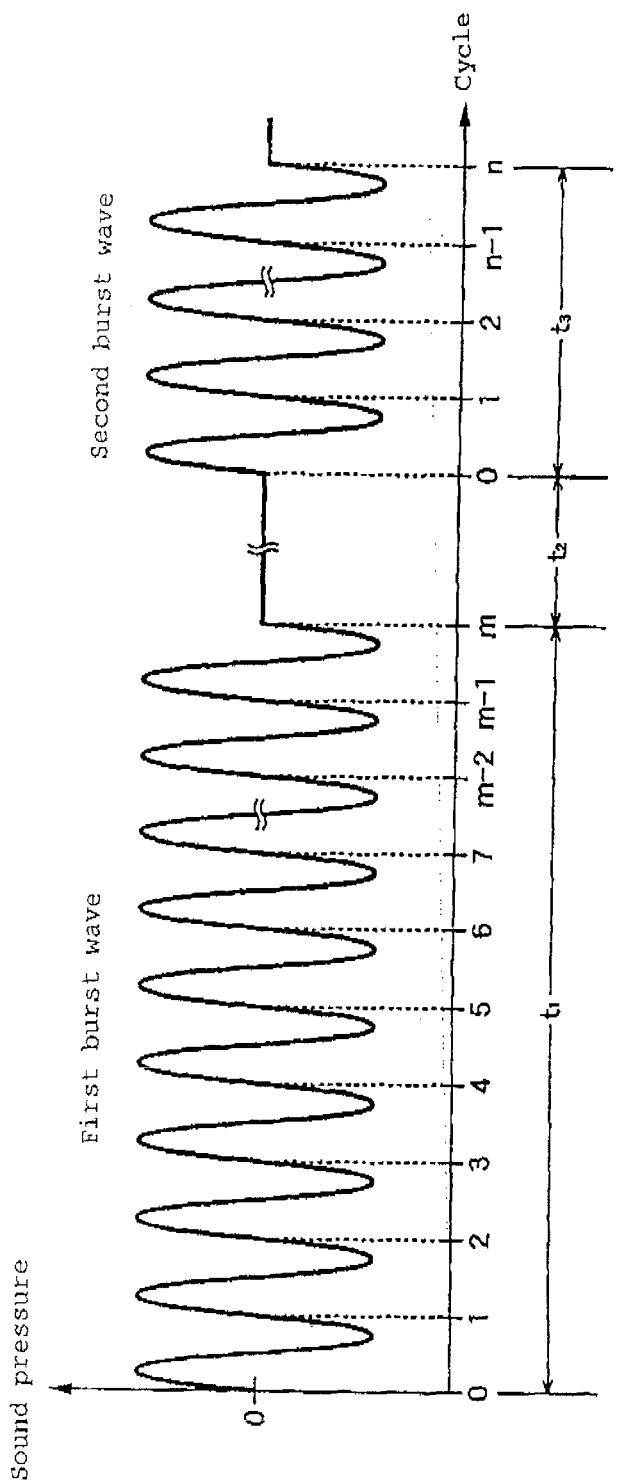
FIG. 2 is a chart showing a sound pressure waveform of an ultrasonic wave transmitted in the ultrasonic imaging apparatus according to the first embodiment of the invention.

The ultrasonic beam transmitted from the ultrasonic probe 20 is set to generate such a continuous wave as to form a sound pressure waveform shown in FIG. 2 in a convergent region.

As shown in FIG. 2, first of all, a first burst wave continuing for m (m is an integer of 10 or more) cycles (wavelengths) is transmitted in order to activate the chaotic oscillation or branch phenomenon of a micro bubble. In order to obtain an ultrasonic image, then, a second burst wave continuing for n (n is an integer which is 4 or more and less than 10) cycles (wavelengths) is transmitted. In the first burst wave the number m of continuing cycles is preferably set to be 10 or more and 50,000 or less, and more preferably, 10 or more and 100 or less. In the second burst wave, moreover, the number n of continuing cycles is preferably set to be 4 or more and 6 or less.

The length of the first burst wave is set to be 10 cycles or more because such a period is required for activating the micro bubble. Moreover, the length of the first burst wave is set to be 50,000 cycles or less in consideration of the balance of the efficiency of micro bubble activation and a time required for scanning an ultrasonic wave.

On the other hand, the length of the second burst wave is set to be four cycles or more because sub-harmonics are to be generated easily. Moreover, the length of the second burst wave is set to be less than ten cycles because the space resolution of an obtained ultrasonic image is reduced with the use of an ultrasonic wave continuing for a long period of time.

As shown in FIG. 2, the first burst wave for activating the micro bubble is transmitted for a first period $t_1$ and the transmission of the ultrasonic wave is stopped for a second period $t_2$, and the second burst wave for obtaining an ultrasonic image is transmitted for a third period $t_3$. The second period $t_2$ is set to be 1 msec or more and 1 sec or less, preferably, 10 msec or more and 100 msec or less in consideration of a time required for the ultrasonic wave transmitted for the first period $t_1$ to be reflected and returned by the subject.

Moreover, irradiation intensities of the first and second burst waves have such sound pressures as not to instantaneously break a contrast agent (micro bubbled). More specifically, it is desirable that the sound pressures of the first and second burst waves each should be 10 kPa or more and 200 kPa or less, particularly, 30 kPa or more and 100 kPa or less. Consequently, the micro bubble is not broken instantaneously. Therefore, the micro bubble injected in the subject can be continuously observed in a real time.

Figure 3:
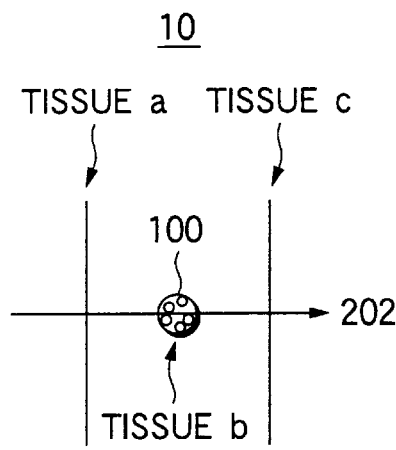
FIG. 3 is a diagram showing a state in which the transmitted ultrasonic wave is incident on a subject in the ultrasonic imaging apparatus according to the first embodiment of the invention.

An ultrasonic wave having such a waveform is incident on the tissue of the subject shown in FIG. 3 and an ultrasonic wave (echo) reflected from the subject 10 is incident on the ultrasonic probe. As shown in FIG. 3, the subject 10 includes tissues a, b and c. For example, the tissues a and c are cells and the tissue b is a blood vessel. The micro bubble 100 is injected into the tissue b. A sound ray 202 of the transmitted wave penetrates through the tissues a, b and c and a part of the transmitted wave is reflected by two walls of the tissues a and b and the tissue c. Moreover, another part of the transmitted wave is reflected by the micro bubble 100 present in the tissue b to generate a sub-harmonic component. By specifying a time required from the transmission of a transmitted wave to the receipt of a reflected wave, it is possible to selectively acquire image information in different positions in a direction of a depth.

Figure 4:
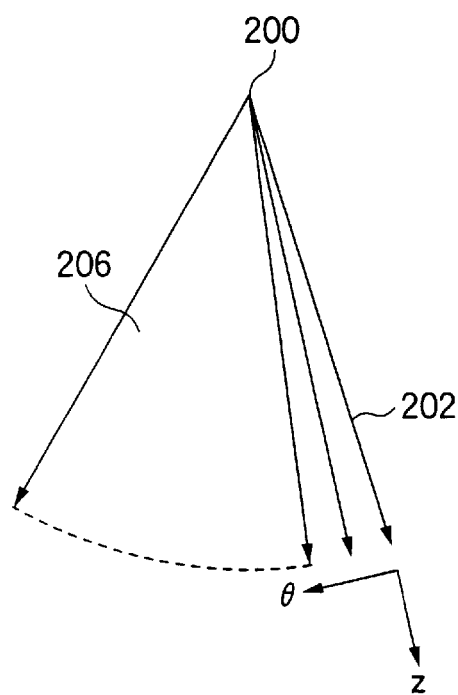
FIG. 4 is a diagram showing an example of sound ray scanning in the ultrasonic imaging apparatus according to the first embodiment of the invention.

The transmission of the ultrasonic beam is repetitively carried out at a predetermined time interval in response to the transmitting timing signal generated by the transmitting timing generating circuit 322 shown in FIG. 1. The azimuth of the ultrasonic beam is sequentially changed by the transmitting beam former 321. Consequently, the inside of the subject 10 is scanned by a sound ray formed by the ultrasonic beam. More specifically, the direction of the sound ray is sequentially changed in the subject 10. The transmitting and receiving section 30 having such a structure carries out a scan shown in FIG. 4, for example. In FIG. 4, the ultrasonic beam (the sound ray 202) extended in a z direction from a radiant point 200 scans a fan-shaped two-dimensional region 206 in a θ direction and carries out a so-called sector scan.

Figure 5:
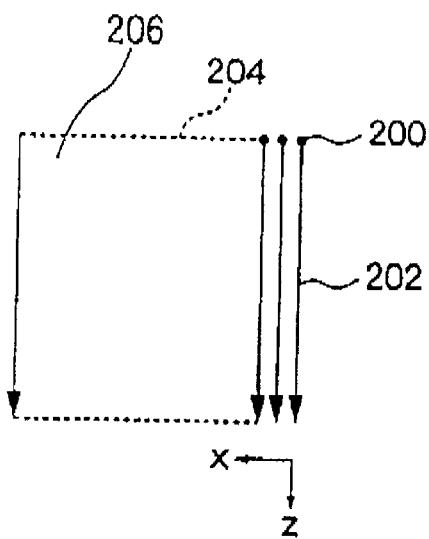
FIG. 5 is a diagram showing another example of the sound ray scanning in the ultrasonic imaging apparatus according to the first embodiment of the invention.

On the other hand, in the case in which the transmitting and receiving apertures are to be formed by using a part of an ultrasonic transducer array, they are sequentially moved along the ultrasonic transducer array so that a scan shown in FIG. 5 can be carried out, for example. In FIG. 5, the sound ray 202 extended in the z direction from the radiant point 200 is moved in parallel along a locus 204 on a straight line, thereby scanning the rectangular two-dimensional region 206 in an x direction and carrying out a so-called linear scan.

Figure 6:
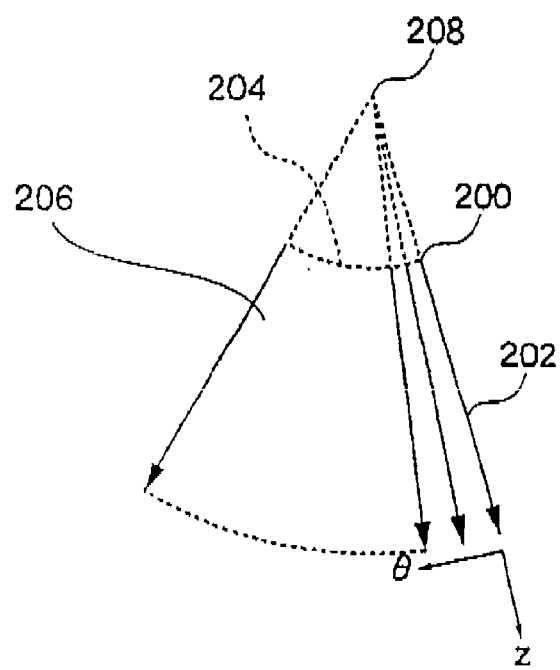
FIG. 6 is a diagram showing a further example of the sound ray scanning in the ultrasonic imaging apparatus according to the first embodiment of the invention.

Moreover, in the case in which the ultrasonic transducer array is a so-called convex array formed along a circular arc protruded in a direction of ultrasonic wave transmission, a scan shown in FIG. 6 can be carried out by the same sound ray scan as the linear scan, for example. In FIG. 6, the radiant point 202 of the sound ray 202 is moved along the circular locus 204 by setting a divergent point 208 to be a center, and the fan-shaped two-dimensional region 206 is scanned in the θ direction to carry out a so-called convex scan.

The first burst wave and the second burst wave may be alternately irradiated for each sound ray. Moreover, the inside of one two-dimensional region maybe scanned by the first burst wave and the inside of the same two-dimensional region may be scanned by the second burst wave to obtain an ultrasonic image. Alternatively, while the inside of a plurality of two-dimensional regions may be scanned by the second burst wave to obtain an ultrasonic image, it may be properly scanned by the first burst wave. In any case, it is desirable that the first burst wave and the second burst wave should be alternately irradiated and a non-transmission period of 1 msec to 1 sec, preferably 10 msec to 100 msec should be provided therebetween.

Returning to FIG. 1, the receiving beam former 331 is connected to a waveform processing section 400 of a signal processing section 40. The waveform processing section 400 separates a fundamental wave component and a sub-harmonic component from an echo receiving signal for each input sound ray, and outputs the fundamental wave component to a fundamental wave processing section 401 and outputs the sub-harmonic component to a sub-harmonic processing section 402. The fundamental wave processing section 401 and the sub-harmonic processing section 402 process the input fundamental wave component and subharmonic component and outputs them to an image processing section 403, respectively. The image processing section 403 generates a fundamental wave B mode image obtained by luminance modulation with an intensity of the fundamental wave based on the fundamental wave component and generates a sub-harmonic B image obtained by luminance modulation with an intensity of the sub-harmonic component based on the sub-harmonic component.

The waveform processing section 400 extracts the sub-harmonic component from a detection signal input from the receiving beam former 331 by using a band-pass filter. A frequency of the sub-harmonic component to be extracted is preferably 1/2 or 3/2 of a frequency of the fundamental wave and more preferably 3/2 of the frequency of the fundamental wave.

The fundamental wave processing section 401 detects a fundamental wave echo obtained by a received wave (which is a received weave having the same frequency as the basic frequency of a transmitted wave), and logarithmically amplifies and envelope detects the fundamental wave echo, thereby acquiring a signal indicative of an intensity of an echo in each reflecting point on the sound ray, that is, an A scope signal. Moreover, the fundamental wave processing section 401 forms B mode image data by setting an instantaneous amplitude at each time of the A scope signal to be each luminance value.

Figure 7:
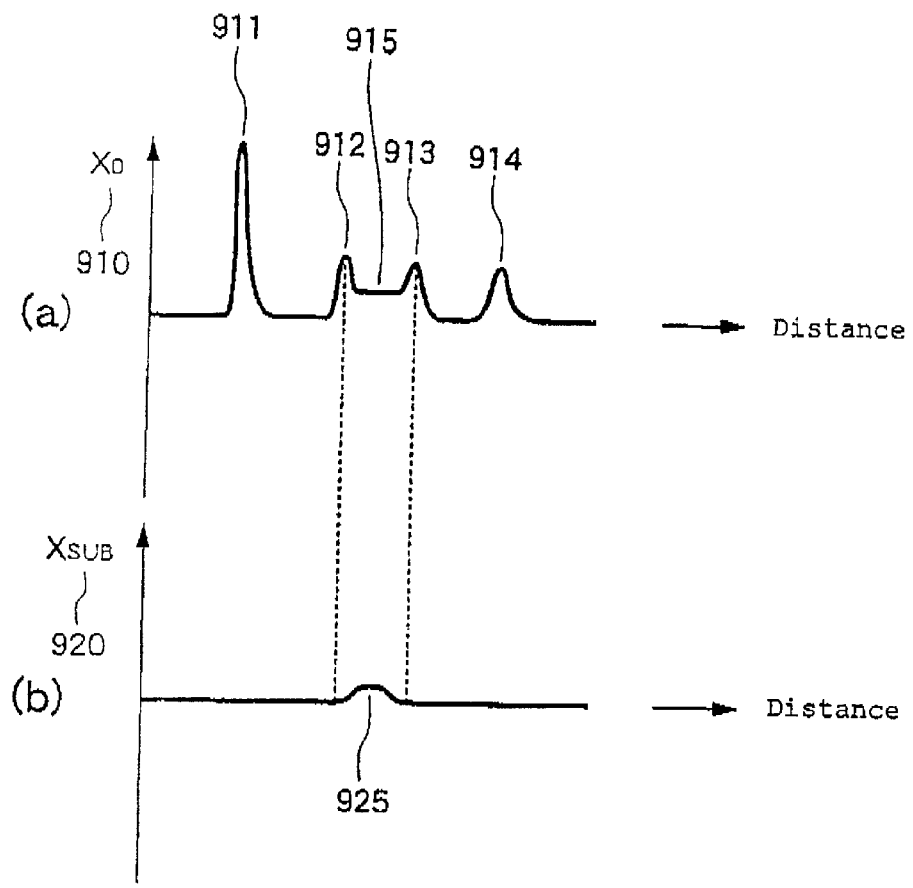
FIG. 7 is a chart showing, as a luminance signal, one-dimensional image data generated in a method of processing a signal of an ultrasonic diagnosis image according to the first embodiment of the invention.

One-dimensional image data generated based on the fundamental wave echo are indicated as a luminance signal $X_0$910 in FIG. 7(a). A scattering 911 of the tissue a, scatterings 912 and 913 of two walls of the tissue b, a scattering 914 of the tissue c and a scattering 915 of a micro bubble injected into the tissue b shown in FIG. 3 are extracted from the luminance signal $X_0$ 910.

The sub-harmonic processing section 402 (FIG. 1) logarithmically amplifies and envelope detects the sub-harmonic echo obtained form the received wave, thereby acquiring a signal indicative of the intensity of the echo in each reflecting point on a sound ray, that is, an A scope signal. Moreover, the sub-harmonic processing section 402 forms B mode image data by setting an instantaneous amplitude at each time of the A scope signal to be each luminance value.

One-dimensional image data generated based on the sub-harmonic echo are indicated as a luminance signal $X_{SUB}$ 920 in FIG. 7(b). A sub-harmonic signal 925 of a micro bubble injected into the tissue b shown in FIG. 3 is extracted from the luminance signal $X_{SUB}$ 920.

Returning to FIG. 1, the fundamental wave processing section 401 and the sub-harmonic processing section 402 are connected to the image processing section 403. The image processing section 403 generates a plurality of B mode images based on the B mode image data input from the fundamental wave processing section 401 and the sub-harmonic processing section 402, respectively. This operation will be described below in detail.

The B mode image data based on the fundamental wave echo and the sub-harmonic echo which are input for each sound ray from the fundamental wave processing section 401 and the sub-harmonic processing section 402 are stored in a sound ray data memory of the image processing section 403, respectively. Each sound ray data space is formed in the sold ray data memory.

The sound ray data space in the sound ray data memory is converted from data of the sound ray data space into data of a physical space through the scanning conversion of a digital scan converter (DSC) 404. The image data converted by the DSC 404 is stored in an image memory 405. The image memory 405 stores the image data of the physical space. The data of the sound ray data memory and the image memory 405 are subjected to predetermined data processings through an image processing processor, respectively.

A display section 50 is connected to the image memory 405. The display section 50 displays an image based on the image data of the physical space stored in the image memory 405. It is desirable that the display section 50 can display a color image.

The transmitting and receiving section 30 and the signal processing section 40 are connected to a control section 60. The control section 60 serves to give a control signal to each section, thereby controlling an operation thereof. Moreover, various notification signals from these sections are input to the control section 60. Ultrasonic imaging is carried out under control of the control section 60. Furthermore, the control section 60 includes an operating section. The operating section is operated by an operator and a desired command or information is input to the control section. The operating section is constituted by an operation panel comprising a keyboard or other operating tools, for example.

Each of the fundamental wave processing section 401 to the image processing section 403 may be constituted by an analog circuit or a digital circuit. Alternatively, it may be constituted by a software and a CPU. In that case, the control section 60 including the CPU processes a detection signal based on an ultrasonic processing program recorded in a recording medium 70. A floppy disk, a hard disk, an MO, an MT, an RAM, a CDROM or a DVDROM corresponds to the recording medium 70.

Next, the operation of the ultrasonic imaging apparatus according to the embodiment will be described.

An operator causes the ultrasonic probe 20 to abut on a desired portion of the subject 10 and operates the operating section, thereby carrying out imaging. An ultrasonic wave is transmitted and received while a sound ray is sequentially scanned under control of the control section 60. Thus, the imaging is carried out. For example, the sound ray is sequentially scanned through a sector scan shown in FIG. 4, and at the same time, an ultrasonic beam is transmitted for each sound ray and an echo thereof is received to generate a B mode image based on an echo received wave. As a matter of course, the linear scan or convex scan shown in FIG. 5 or 6 may be carried out.

An ultrasonic beam to be transmitted at this time has the sound pressure waveform shown in FIG. 2, for example, and activates the micro bubble 100 and reliably generates a sub-harmonic echo. B mode image data are formed based on the echo received wave in each sound ray. The B mode image data are formed based on a fundamental wave echo and a sub-harmonic echo respectively and are stored in the sound ray data memory of the image processing section 403.

Figure 8:
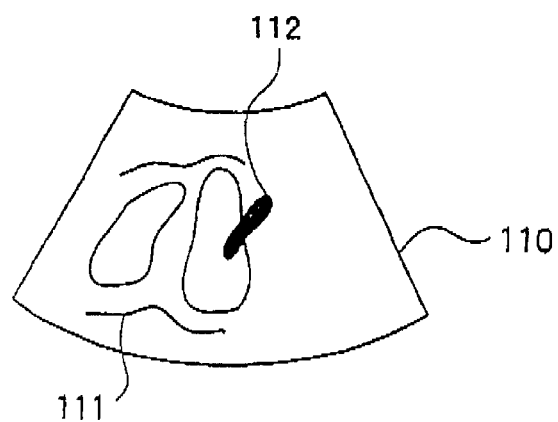
FIG. 8 is a diagram showing an example of a displayed image in the ultrasonic imaging apparatus according to the first embodiment of the invention.

The sound ray data in the sound ray data memory are scanned and converted by the DSC 404 and are written to the image memory 405, respectively. The operator operates the operating section to display these B mode images on the display section 50. For example, as shown in FIG. 8, a synthesis image of a tomogram image 111 of a tissue obtained based on the fundamental wave echo and an image 112 obtained based on the sub-harmonic echo of the micro bubble is displayed on a display 110 of the display section.

Next, a second embodiment of the invention will be described. In the embodiment, a difference between a detection signal and a delayed detection signal is obtained in a waveform processing section in place of the use of the band-pass filter in the first embodiment in order to extract a sub-harmonic component from the detection signal of an ultrasonic echo detection signal.

A method of extracting a sub-harmonic signal according to the embodiment will be described with reference to FIG. 9.

Figure 9:
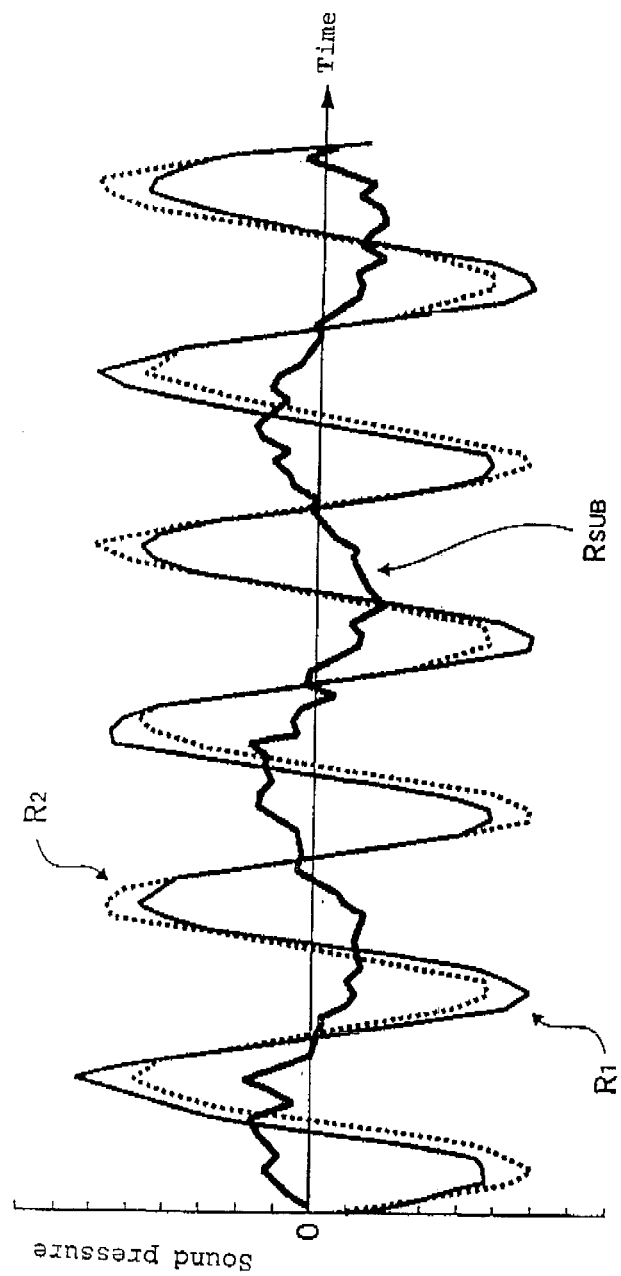
FIG. 9 is a waveform diagram for explaining a processing of a detection signal according to a second embodiment of the invention.

An echo of a micro bubble has a waveform $R_1$ shown in FIG. 9. The waveform $R_1$ is delayed by a fundamental period $\tau$ of a transmitted wave to create a waveform $R_2$. Next, a difference between the waveform $R_1$ and the waveform $R_2$ is calculated to obtain a waveform $R_{SUB}$ of the sub-harmonic signal. The echo of the transmitted ultrasonic wave is formed by the sum of a fundamental wave, a harmonic and the sub-harmonic signal. Since the fundamental wave and the harmonic have waveforms in which the fundamental cycle $\tau$ of the transmitted wave is set to be a repetition unit, they are removed by the signal processing. As a result, only the sub-harmonic signal remains.

Figure 10:
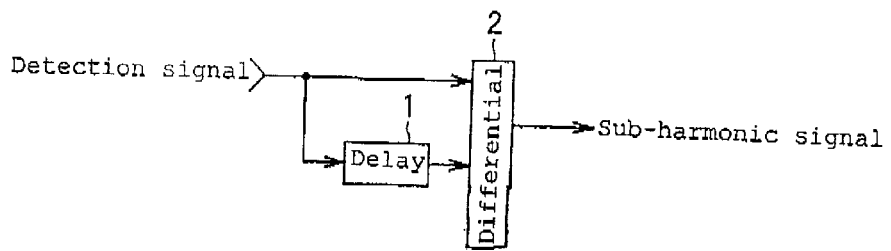
FIG. 10 is a block diagram showing apart of the structure of a waveform processing section according to the second embodiment of the invention.

FIG. 10 shows a part of the structure of the waveform processing section according to the embodiment. In FIG. 10, a delay circuit 1 delays a detection signal by a transmitting fundamental cycle $\tau$. A differential circuit 2 calculates a difference between a detection signal and a delayed detection signal, thereby extracting and outputting a sub-harmonic signal.

Next, a third embodiment of the invention will be described. In the embodiment, two detection signals having a phase difference are obtained by a path difference between a reflecting point of an ultrasonic wave aid a plurality of ultrasonic transducers included in an ultrasonic probe and a difference therebetween is calculated in place of the use of the delay circuit according to the second embodiment in order to extract a sub-harmonic component from the detection signal of an ultrasonic echo.

Figure 11:
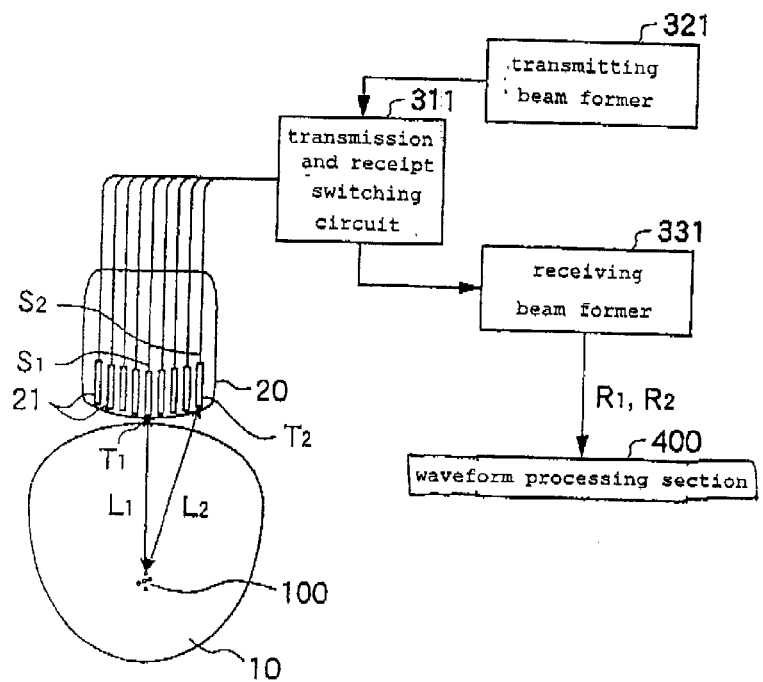
FIG. 11 is a block diagram showing an ultrasonic probe and a peripheral circuit thereof according to a third embodiment of the invention.

As shown in FIG. 11, it is desirable that a plurality of ultrasonic transducers 21 included in the ultrasonic probe 20 should be arranged with a step in a receiving direction. A receiving beam former 331 selects at least two ultrasonic transducers from the ultrasonic transducers 21, thereby acquiring two detection signals having phases shifted by a time equivalent to one cycle of a transmitted ultrasonic wave. For example, a detection signal $S_1$ is obtained from an ultrasonic transducer $T_1$ and a detection signal $S_2$ is obtained from an ultrasonic transducer $T_2$. A relationship of $L_2-L_1=\lambda$ is obtained, wherein one wavelength of the transmitted ultrasonic wave is represented by $\lambda$, a distance from a reflecting point of a subject 10 to the ultrasonic transducer $T_1$ is represented by $L_1$, and a distance from the reflecting point of the subject 10 to the ultrasonic transducer $T_2$ is represented by $L_2$.

Furthermore, the receiving beam former 331 may give a time difference to a plurality of received echoes to adjust a phase, and may then add them to for an echo detection signal along a sound ray, that is, to carry out the beam forming of a received wave. The receiving beam former 331 processes the detection signals $S_1$ and $S_2$ to finally output a first detection signal $R_1$ and a second detection signal $R_2$ which have phases shifted by a time equivalent to one cycle of a transmitted ultrasonic wave. In a waveform processing section 400, a difference between the first detection signal $R_1$ and the second detection signal $R_2$ is obtained, thereby acquiring a waveform $R_{SUB}$ of the sub-harmonic signal shown in FIG. 8 in the same manner as in the second embodiment.

While the example in which the sub-harmonic echo is utilized to carry out B mode imaging has been described in these embodiments, ultrasonic imaging is not restricted to the B mode imaging but a Doppler shift of a sub-harmonic echo may be utilized to pick up a dynamic image.

The characteristic aspects of the ultrasonic scatterer of the invention are described in more detail by reference to Examples. Materials, amounts used, proportions, processing contents, processing procedures, etc. may properly be changed within the spirit of the invention. Therefore, the scope of the invention is not construed limitatively by the specific embodiments shown below.

(1) Apparatus and method for evaluating subharmonics

Figure 12:
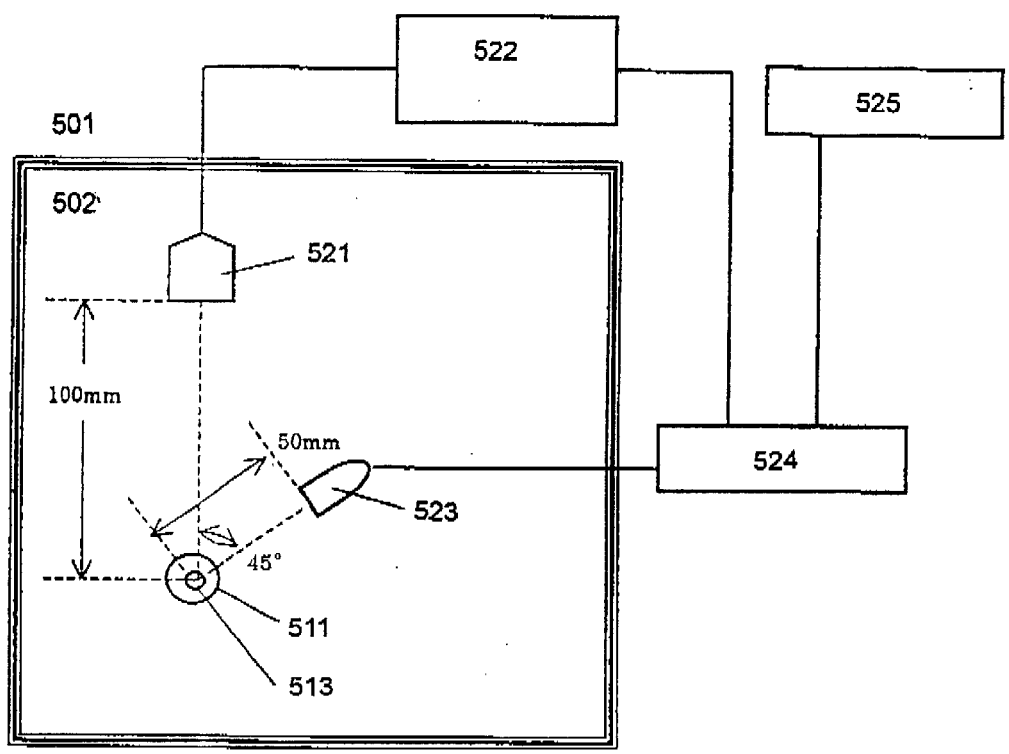
FIG. 12 is a diagram showing the apparatus for measuring ultrasonic scattering used in Example 1.

The apparatus for measuring ultrasonic scattering used for evaluation of subharmonics is shown in FIG. 12.

Pure water 502 was charged in a water bath 501, and a transducer 521, a hydrophone 523, and an agar-made cell 511 were sunk into the pure water. An ultrasonic scatterer dispersion 513 was injected into the inside of the agar cell 511.

To the transducer 521 were sent signals from the arbitrary wave form-generating apparatus 522 to oscillate transmission ultrasound. The arbitrary wave form-generating apparatus 522 transmited signals to the transducer 521 and, at the same time, sent a trigger signal to an oscilloscope 524. The oscilloscope 524 took the received signals the hydrophone 523 by the trigger signal transmitted from the arbitrary wave form-generating apparatus 522. A computer 525 connected to the oscilloscope 524, and analyzed the wave form received by the hydrophone. Here, the transducer 521 was a 3.5 MHz wide-band, focus-less type A381S made by Nihon Panametrics K.K., the arbitrary wave form-generating apparatus 522 was AWG2021 made by Tectronics K.K., the hydrophone 523 was a large-diameter PPPPPPVDF hydrophone made by Toray Tecno K.K., and the oscilloscope 524 was Bringo made by Iwasaki Tsusinki K.K. As the agar cell 511, that prepared by making a 2.5 mmØ hole in Dentroid Middle Blue (8 mmØ) made by K.K. Dentonics was used.

As the method for evaluating subharmonics, the ultrasonic scatterer was injected into the agar cell 511 and the receiving signal according to the above-described method were subjected to high speed Fourier transformation, and the ratio of 1/2 subharmonic component to secondary harmonic component (dB) (response to transmitting wave) was determined, which was taken as an evaluating value.

(2) Photographing of ultrasonic scatterer after irradiation with ultrasound:

A photograph of the ultrasonic scatterer after irradiated with ultrasound (a sample prepared by diluting OPTISON made by Mallonckrodt Inc. with pure water to 1/100) (FIG. 14) was taken by injecting the sample into the gap of Sekisui Kenkyo Plate made by Sekisui Kagaku Kogyo K.K. and photographing using a degital HD Microscope VH-700 made by K.K. Kiense to which a zoom lens VH-Z450 was mounted.

Figure 14:
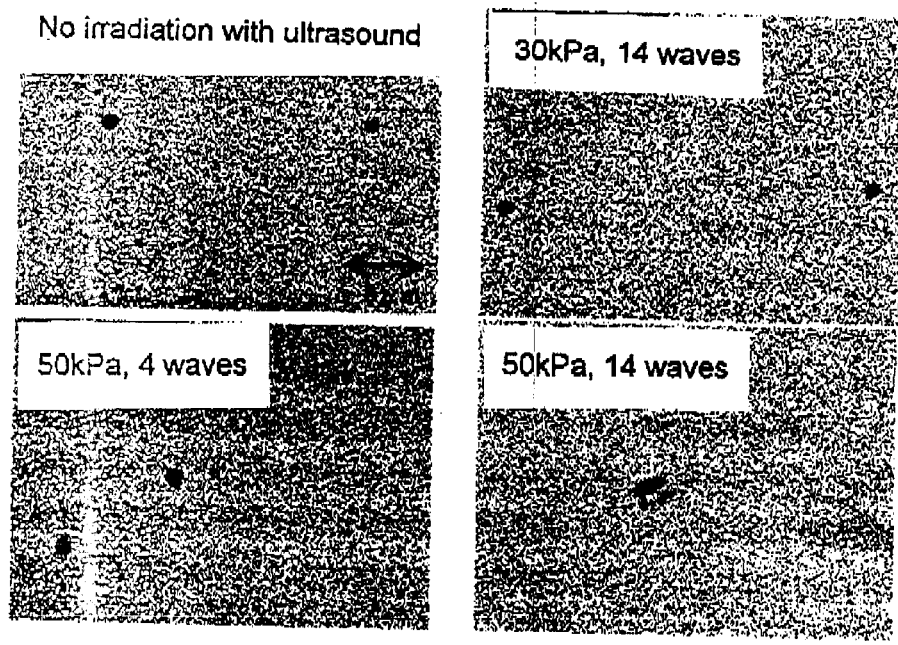
FIG. 14 is a photograph of an optical microscope of the ultrasonic scatterer (OPTISON) after irradiation with ultrasound.

It is seen from FIG. 14 that particles gathered at a 50 kPa, 14 wave which is a critical condition for the subharmonics to appear. It is known that primary and secondary Bjerknes forces work as attractive force between the bubbles of the ultrasonic scatterer oscillating, upon irradiation with the ultrasound, with a distance smaller than the co-oscillation particle size and at the same phase with the irradiated ultrasound (Ida, et al., Nicchoi Kisogijutu Kentokai Shiryo, Vol. 100, No. 2, p. 5, Sep. 4, 2000). In the above-described measuring system, too, the same function were inferred to have worked to gather the bubbles. The oscillation behavior of the bubble aggregates is known to be different from the behavior of a single bubble (Matsumoto, Nicchoi Kosogijutsu Kentokai Shiryo, Vol.100, No. 2, p.1, Sep. 4, 2000). That is, it is inferred that, by irradiation with ultrasound, the bubble aggregates were formed and, as a result, a caotic factor became stronger in the oscillation behavior, thus subharmonics having started to appear.

(3) Preparation of solid fine particles

1) Preparation of an SBR latex 70.5 parts by weight of styrene, 26.5 parts by weight of butadiene and 3 parts by weight of acrylic acid were emulsion polymerized using ammonium persulfate as a polymerization initiator and an anionic surfactant as an emulsifying agent, followed by aging at 80° C. for 8 hours. Then, the reaction mixture was cooled to 40° C., then adjusted to pH 7.0 with aqueous ammonia, followed by adding thereto Sandet BL made by Sanyo Kasei K.K. to a concentration of 0.22%. Subsequently, 5% sodium hydroxide aqueous solution was added thereto to adjust the pH to 8.3 and, further, aqueous ammonia was added thereto to adjust the pH to 8.4. Molar ratio of $Na^+$ ion to $NH_4^+$ ion used was 1:2.3. Further, 0.15 ml of a 7% aqueous solution of sodium salt of benzoisothazolinone was added thereto per kg of the solution to prepare an SBR latex.

The resultant SBR latex [-Sr (70.5)-Bu (26.5)-AA (3)-] had a Tg of 23° C., an average particle size of 0.1 μm, a concentration of 43% by weight, an equilibrium water content of 0.6% at25° C. and 60% in relative humidity, an ion conductivity of 4.2mS/cm (measured at 25° C. by a conductivity meter CM-30S made by Toa Denpa Kogyo K.K. using the latex solution (43% by weight)), and a pH of 8.4. This SBR dispersion was diluted with pure water to a concentration of 8% by weight to use as an SBR latex solution hereinafter.

2) Preparation of PGALA particles:

10 ml of a 20% by weight solution of poly (DL-lactide-co-glycolide) (PGALA:50:50; molecular weight: 50,000 to 75,000) made by Aldrich Co. In methylene chloride was added to 100 ml of a 1% aqueous solution of polyvinyl alcohol, PVA-217, made by Kuraray K.K., emulsified in a homogenizer, then evacuated to evaporate methylene chloride, and filtered through a Fuji Film Micro filter AstroPore (pore size; 0.45 μm) made by Fuji Photo Film Co., Ltd. to obtain PGALA particles. The average particle size of the resultant particles was determined to be 0.1 μm based on the picture obtained by a transmission type electron microscope.

3) Preparation of GEL particles:

10 ml of a 10% by weight aqueous solution of gelatin (GEL) was mixed with 100 ml of ethyl acetate at 40° C., and emulsified in a homogenizer, followed by adding thereto 1 ml of 10% by weight aqueous solution of glutaraldehyde and mixing, then leaving the mixture for 3 hours. Further, this dispersion was added to 100 ml of water and mixed, followed by evaluating the system to evaporate ethyl acetate and filtering through a Fuji Film Micro Filter AstroPore (pore size: 0.45 μm) made by Fuji Photo Film Co., Ltd. to obtain GEL particles. The average particle size of the resultant particles was measured to be 0.2 μm with a laser-diffraction type particle size distribution-measuring apparatus SALD-2000A.

(4) Preparation of gas-containing particles:

1) Preparation of $C_3F_8$ bubbles having an albumin shell.

5 g of human serum albumin (ALB) was dissolved in 100 ml of a physiological salt solution, and a $C_3F_8$ gas was injected thereinto at a lineal speed of 20 m/sec through a 20 μm nozzle. Coarse particles of the resultant shelled bubbles were removed by means of a Cyclopore Membrane (hydrophilic polycarbonate membrane type; pore size: 10 μm) made by Whatman® to obtain CA01. A sample obtained by adding 0.1 g of glutaraldehyde (GA) was referred to as CA02.

2) Preparation of $C_3F_8$ bubbles having a phospholipid:

24.9 mg of dipalmitoylphosphatidylcholine, 2.8 mg of sodium dipalmitoylphosphatidylate and 2.3 mg of dipalmitoylphosphatidylethanol amine were dispersed in 6 ml of a physiological salt solution, and a a $C_3F_8$ gas was injected thereinto at a lineal speed of 20 m/sec through a 20 μm nozzle. Coarse particles of the resultant shelled bubbles were removed by means of a Cyclopore Membrane (hydrophilic polycarbonate membrane type; pore size: 10 μm) made by Whatman® to obtain CA03.

3) Measurement of average particle size:

The resultant particles and OPTISON were injected into the Sekisui Kenkyo Plate made by Sekisui Kagaku Kogyo K.K., and images photographed using a degital HD microscope VH-700 with a zoom lens VH-Z450 made by Keyence Corp. were analyzed using Win ROOF made by Mitani Shoji K.K. under the condition of automatically separating circles. The results thus obtained are shown in Table 1.

TABLE 1

| Scatterer | Shell Material | Average Particle Size (μm) |
|---|---|---|
| OPTISON | Heat-denatured ALB | 4.9 |
| CA01 | ALB | 5.5 |
| CA02 | ALB + GA | 4.5 |
| CA03 | Phospholipid | 7.5 |

(5) Preparation of ultrasonic scatterer:

Ultrasonic scatterers of samples 1 to 15 were prepared by mixing the gas-containing particles and/or solid fine particles with water. Kinds of the gas-containing particles and the solid fine particles used in each of the samples are as shown in Table 2. With the samples 1, 3, 4, and 11 to 15, mixing ratio of the solid fine particles:gas-containing particles:water was 1:1:1 (by weight). With the samples 5 to 7, solid fine particles and water were mixed in a ratio of 1:2 (by weight). Further, with the samples 2 and 8 to 10, the gas-containing particles and water were mixed in a ratio of 1:2 (by weight).

Figure 13:
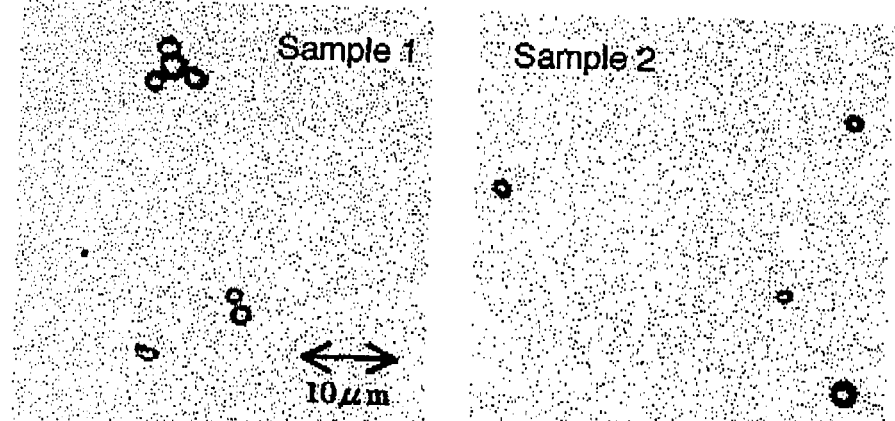
FIG. 13 is a photograph of a microscope of the ultrasonic scatterers of the samples 1 and 2 in Example.

(6) Evaluation of particle state:

Microscopic pictures of the samples 1 and 2 are shown in FIG. 13. As is apparent from the microscopic picture of the sample 1 of the invention, the particles do not form an aggregate with an intermediate layer.

The ultrasonic scatterers of samples 1 to 15 were respectively injected into the Sekisui Kenkyo Plate made by Sekisui Kagaku Kogyo K.K., and were photographed using a digital HD microscope VH-700 with a zoom lenz VH-Z450 made by Keyence Corp. The images thus photographed were analyzed with respect to central coordinates using Win ROOF made by Mitani Shoji K.K. The ratio of particles that have a center-to-center distance between the first particle and the nearest particle of 0.01 μm to 10 μm and a center-to-center distance between the first particle and the second nearest particle of 0.01 μm to 10 μm [neighboring (adjacent) ratio of three particles] and the linearity of the positions of the centers of the particles judged to form an aggregate in the measurement of neighboring ratio with three particles were evaluated. In addition, the neighboring ratio with three particles in the case of diluting with pure water so that the distance between the particles became 1 mm (dilute A neighboring ratio) was also measured. The results thus obtained are shown in Table 2.

(7) Measurement of scattering ultrasound:

Table 2 shows the results of measuring ultrasound response of the samples 1 to 15 diluted to 1/50 with pure water according to the manner described in (1) above under the conditions of 50kPa and 4 wave burst. With the samples of the invention, generation of subharmonics was observed.

TABLE 2 (A)

| Sample | Materials Gas-containing Particles | Materials Solid Fine Particles | State of Particles Three Particles Neighboring Ratio | State of Particles Diluted Neighboring Ratio | Lineality | Subharmonics | Notes |
|---|---|---|---|---|---|---|---|
| 1 | OPTISON | SBR | 50% | 40% | 20% | generated (+5) | Present invention |
| 2 | OPTISON | — | 5% | 2% | 95% | not generated | Comparative Example |
| 3 | OPTISON | PGALA | 40% | 30% | 30% | generated (±0) | Present invention |
| 4 | OPTISON | GEL | 40% | 20% | 70% | generated (−5) | Present invention |
| 5 | — | SBR | — | — | — | not generated | Comparative Example |
| 6 | — | PGALA | — | — | — | not generated | Comparative Example |
| 7 | — | GEL | — | — | — | not generated | Comparative Example |
| 8 | CA01 | — | 10% | 2% | 95% | not generated | Comparative Example |
| 9 | CA02 | — | 15% | 5% | 93% | not generated | Comparative Example |
| 10 | CA03 | — | 5% | 1% | 99% | not generated | Comparative Example |
| 11 | CA01 | PGALA | 40% | 30% | 30% | generated (+5) | Present invention |
| 12 | CA02 | GEL | 80% | 70% | 10% | generated (−5) | Present invention |
| 13 | CA03 | SBR | 40% | 30% | 60% | generated (−5) | Present invention |
| 14 | CA03 | PGALA | 50% | 50% | 20% | generated (+5) | Present invention |
| 15 | CA03 | GEL | 30% | 20% | 70% | generated (−5) | Present invention |

Note) Numerals within the parentheses in the column of "Subharmonics" mean the ratio of (1/2 subharmonic)/(secondary harmonic) (unit: dB).

Subharmonics were evaluated with respect to the sample 1 of the invention diluted with pure water to 1/50 and a comparative sample, OPTISON made by Mallonckrodt Inc., diluted with pure water to 1/100 changing sound pressure and burst wave number, and results thus obtained are shown in Table 3. It was confirmed that, in comparison with the comparative sample, the sample of the invention showed a stronger subharmonics and generated subharmonics at a less sound pressure and a less burst wave number. Reduction in sound pressure serves to prevent destruction of the ultrasonic scatterer and enables real-time imaging. Actually, it was confirmed with an optical microscope that the bubbles contained in the ultrasonic scatterer were not destroyed after generation of subharmonics under the conditions of 50 kPa and 4 waves. In addition, reduction in the burst wave number serves to improve space resolution.

TABLE 3

| Sound Pressure (kPa) | Wave Number | Subharmonics OPTION | Subharmonics Sample 1 |
|---|---|---|---|
| 20 | 70 | not generated | not generated |
| 30 | 54 | not generated | not generated |
| 30 | 70 | generated (−5) | generated (+10) |
| 40 | 4 | — | not generated |
| 40 | 14 | not generated | generated (−5) |
| 50 | 4 | not generated | generated (+5) |
| 50 | 14 | generated (−5) | generated (±0) |
| 50 | 70 | generated (±0) | — |

TABLE 3-continued

| Sound Pressure (kPa) | Wave Number | Subharmonics OPTION | Subharmonics Sample 1 |
|---|---|---|---|
| 100 | 4 | not generated | generated (+10) |
| 200 | 4 | generated (−5) | generated (+10) |

Note) Numerals within the column of "Subharmonics" mean the ratio of (½subharmonic)/(secondary harmonic) unit: dB).

As has been described hereinbefore, the invention can realize an ultrasonic scatterer highly ensuring generation of subharmonic echo under the condition that the bubbles are not destroyed. Thus, the ultrasonic scatterer of the invention is useful as an ultrasonic constant agent.

According to the invention, an ultrasonic wave continuing for ten cycles or more is transmitted to the subject, thereby activating the chaotic oscillation or branch phenomenon of a contrast agent (a micro bubble) to increase a probability of the generation of a sub-harmonic component and an ultrasonic wave continuing for four cycles or more and less than ten cycles is transmitted to the subject, thereby detecting a sub-harmonic component included in an ultrasonic echo at a speed close to a real time. Thus, it is possible to obtain an image having an excellent space resolution.

The entire disclosure of each and every foreign patent application from which the benefit of foreign priority has been claimed in the present application is incorporated herein by reference, as if fully set forth.

What is claimed is:

1. An ultrasonic scatterer comprising gas-containing particles having an average particle size of 0.01 $\mu$m to 10 $\mu$m, wherein, considering three adjacent particles including a first particle, the nearest particle to the first particle and the second nearest particle to the first particle, 20% to 100% by number of the total gas-containing particles satisfy that the three adjacent particles have a center-to-center distance between the first particle and the nearest particle of 0.01 $\mu$m to 10 $\mu$m, and a center-to-center distance between the first particle and the second nearest particle of 0.01 $\mu$m to 10 $\mu$m, wherein, when diluted with pure water so that the average particle-to-particle distance of the gas-containing particles becomes 1 mm, 10% to 100% by number of the total gas-containing particles satisfy that the three adjacent particles have a center-to-center distance between the first particle and the nearest particle of 0.01 $\mu$m to 10 $\mu$m and a center-to-center distance between the first particle and the second nearest particle of 0.01 $\mu$m to 10 $\mu$m.

2. An ultrasonic scatterer comprising gas-containing particles having an average particle size of 0.01 $\mu$m to 10 $\mu$m, wherein the gas-containing particles form particle aggregates including 3 to 100 continuous gas-containing particles, with the center-to-center distance between the gas-containing particles in the aggregates being 0.01 $\mu$m to 10 $\mu$m.

3. The ultrasonic scatterer according to claim 2, wherein the aggregates do not define a straight line when a line is drawn by connecting the centers of respective particles in the aggregates.

4. The ultrasonic scatterer according to claim 2, wherein, when diluted with pure water so that the average particle-to-particle distance of the gas-containing particles becomes 1 mm, 10% to 100% by number of the total gas-containing particles satisfy that the three adjacent particles have a center-to-center distance between the first particle and the nearest particle of 0.01 $\mu$m to 10 $\mu$m and a center-to-center distance between the first particle and the second nearest particle of 0.01 $\mu$m to 10 $\mu$m.

5. The ultrasonic scatterer according to claim 2, wherein the first particle and the nearest particle are positioned so as to not form a contact surface in 10 to 100% by number of the total gas-containing particles.

6. The ultrasonic scatterer according to claim 2, wherein the average particle size of the gas-containing particles is equal to or smaller than the center-to-center distance of the gas-containing particles.

7. The ultrasonic scatterer according to claim 1, wherein, in 10 to 100% by number of the total gas-containing particles, the first particle and the nearest particle are positioned so as to not form a contact surface.

8. The ultrasonic scatterer according to claim 1, wherein the average particle size of the gas-containing particles is equal to or smaller than the center-to-center distance of the gas-containing particles.

9. An ultrasonic scatterer comprising:

gas-containing particles having an average particle size of 0.01 $\mu$m to 10 $\mu$m; and at least one of inorganic solid fine particles and organic solid fine particles, each of which has an average particle size of 0.01 $\mu$m to 1 $\mu$m, wherein the inorganic and organic solid fine particles are solid in water.

10. The ultrasonic scatterer according to claim 9, wherein, considering two adjacent particles including a first particle and the nearest particle to the first particle, 20% to 100% of the total gas-containing particles satisfy that the two adjacent particles have a center-to-center distance between the first particle and the nearest particle of 0.01 $\mu$m to 10 $\mu$m.

11. The ultrasonic scatterer according to claim 10, wherein the average particle size of the gas-containing particles is equal to or smaller than the center-to-center distance of the gas-containing particles.

12. The ultrasonic scatterer according to claim 9, wherein, when diluted with pure water so that the average particle-to-particle distance of the gas-containing particles becomes 1 mm, 10% to 100% by number of the total gas-containing particles satisfy that the two adjacent particles have a center-to-center distance between the first particle and the nearest particle of 0.01 $\mu$m to 10 $\mu$m.

* * * * *